United States Patent
Kinghorn et al.

[11] Patent Number: 5,770,139
[45] Date of Patent: Jun. 23, 1998

[54] METHOD AND APPARATUS FOR CONNECTING TUBING TO BARBED CONNECTORS

[75] Inventors: Curtis D. Kinghorn, Minneapolis, Minn.; Roger J. Elgas, Anaheim Hills, Calif.

[73] Assignee: Medtronic, Inc., Minneapolis, Minn.

[21] Appl. No.: 622,778

[22] Filed: Mar. 27, 1996

[51] Int. Cl.[6] .................................................. B29C 61/02
[52] U.S. Cl. .................. 264/230; 264/234; 264/DIG. 71; 422/22
[58] Field of Search ................................. 156/84, 85, 86, 156/91, 294; 264/230, 234, 239, DIG. 71; 422/22, 38; 29/447, 508; 604/283, 905; 285/381.1, 381.3, 381.2, 381.4, 381.5, 909

[56] References Cited

U.S. PATENT DOCUMENTS

| | | | |
|---|---|---|---|
| 3,017,203 | 1/1962 | Macleod | 29/508 |
| 3,210,100 | 10/1965 | Lowles et al. | 285/239 |
| 3,851,896 | 12/1974 | Olson | 239/542 |
| 3,957,382 | 5/1976 | Greuel, Jr. et al. | 285/909 |
| 4,816,221 | 3/1989 | Harvey et al. | 604/905 |
| 5,169,176 | 12/1992 | Brossard | 156/84 |
| 5,340,167 | 8/1994 | Morse | 156/86 |
| 5,531,483 | 7/1996 | Christian et al. | 285/381.4 |

FOREIGN PATENT DOCUMENTS

| | | |
|---|---|---|
| 2207060 | 8/1973 | Germany . |
| 93/17272 | 9/1993 | WIPO . |
| 94/18486 | 8/1994 | WIPO . |

*Primary Examiner*—Richard Crispino
*Attorney, Agent, or Firm*—Harry G. Weissenberger

[57] ABSTRACT

A tight, sterile connection between flexible tubing and a connector on a medical device is produced by pre-assembling the tubing and the connector, heat-shrinking the tubing onto the connector, and then sterilizing the connection while maintaining compression of the tubing against the connector.

2 Claims, 2 Drawing Sheets

METHOD AND APPARATUS FOR CONNECTING TUBING TO BARBED CONNECTORS

FIELD OF THE INVENTION

This invention relates to connections connecting flexible tubing to apparatus such as medical devices, and more particularly to strong, fluid-tight attachment methods using heat-shrinkable materials.

BACKGROUND OF THE INVENTION

Many disposable devices, such as oxygenators, blood pumps and other apparatus commonly used in medical procedures have rigid, barbed polycarbonate connectors to which flexible polyvinyl chloride (PVC) hoses or tubing are connected in use. Conventionally, the user slips the tubing over the barbs of the connector and then secures it in place by cinching a plastic cable tie around the tubing at the connector.

Although this conventional fastening method is satisfactory in most instances, its security is, at least to some extent, dependent upon the skill of the clinical technician assembling the equipment. Consequently, there is still some risk of human error or material weakness leading to failure, leakage or loss of sterility of the connection, particularly if the connection is, perhaps inadvertently, jostled or subjected to stress in a disengaging direction.

SUMMARY OF THE INVENTION

The present invention solves the problem of the prior art by pre-assembling the tubing and the devices at the manufacturing site. This in turn allows novel connection methods to be used to provide a mechanically secure, fluid-tight and sterile connection between the tubing and the barbed connector.

The method contemplated by this invention (which is not restricted to use at the manufacturing site but could, under appropriate circumstances, be used in the field as well) provides a simple, secure attachment of PVC tubing to barbed polycarbonate through the use of heat-shrinkable materials. Some of these materials, generally various types of PVC, can be conventionally formulated to shrink at temperatures higher than the typical sterilization temperature of about 55° C., or to shrink at temperatures lower than sterilization temperatures. The former type exhibits some cold-flow characteristics at sterilization temperatures.

Depending upon the type of heat-shrinkable material used, the invention solves the problem of the prior art in one of two ways: either by using PVC tubing which shrinks at a high temperature, or by using non-shrinkable PVC tubing within a sleeve shrinkable by the sterilization process. In the latter case, the PVC tubing can advantageously be anchored to the heat-shrunk sleeve by the interposition of an anchor member which bites into both the tubing and the sleeve.

DESCRIPTION OF THE PREFERRED EMBODIMENTS

FIG. 1 shows a connection 10 in which a conventional connector 12 is connected to a piece of PVC tubing 14 shrinkable at high heat in accordance with one embodiment of the invention.

Figure 1A:
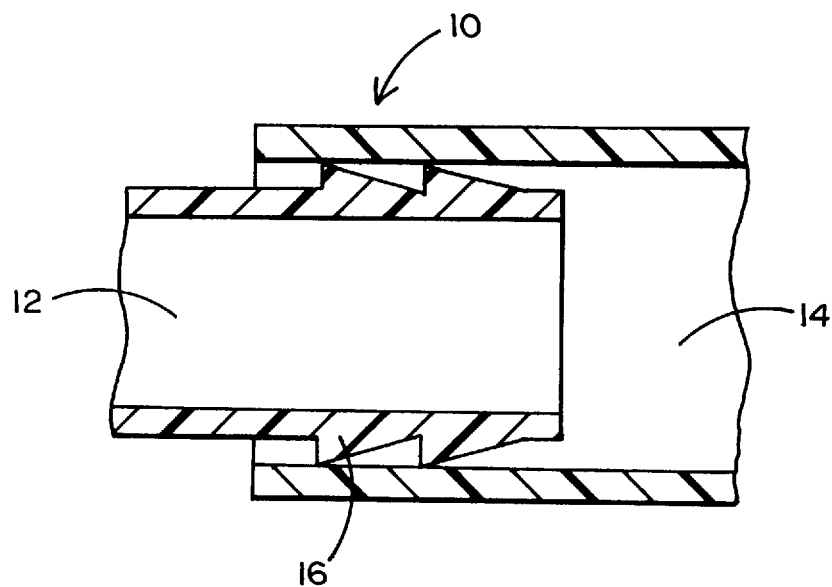
FIGS. 1a and 1b are longitudinal cross sections, respectively, of a connector before and after using one embodiment of the invention.
Figure 1B:
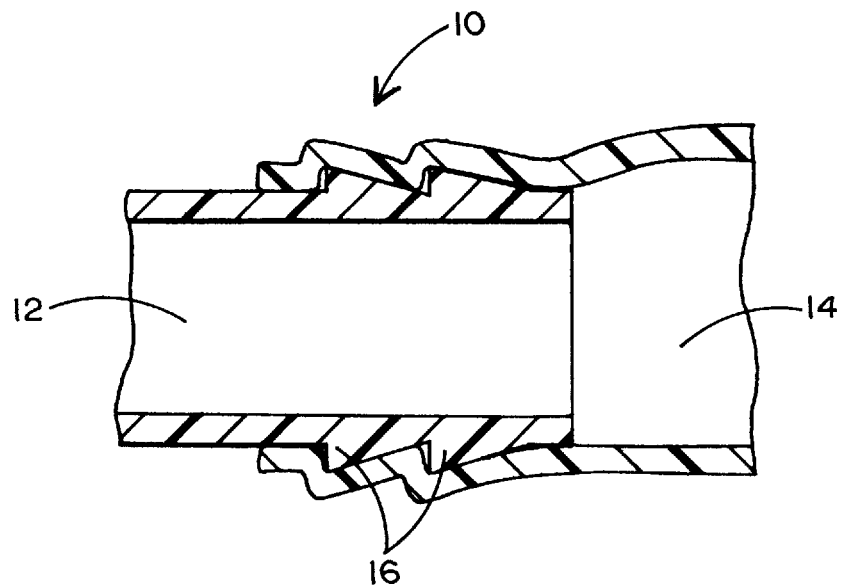

The tubing 14 is initially connected to the connector 12 by slipping it over the barbs 16 of the connector 12 in the conventional manner (FIG. 1a). At this time, the tubing 14 is of uniform diameter and slips easily over the barbs 16. In order to secure the tubing 14 to the connector 12, the tubing end which has been slipped over the connector 12 is heated to about 80° C. At that temperature, the heat-shrink material of which the tubing 14 is made contracts and shrinks into firm contact with the barbs 16 (FIG. 1b). Once so shrunk, the tubing 14 can no longer be removed from the connector 12. If this process is used, it is imperative that only the portion of the tubing 14 which overlies the connector 12 be exposed to shrink temperatures, as any shrinkage of tubing 14 beyond the connector 12 would result in an unacceptable constriction of the tubing's lumen.

The amount of shrinkage of the tubing 14 can be controlled by varying the time and temperature of the heat-shrinking process. In accordance with the invention, it is necessary to overcompress the connection, i.e. to cause the tubing 14 to shrink more tightly onto the connector 12 than it needs to do. The reason for this is that when the equipment is sterilized following the making of the connection, the tubing 14 becomes heated to about 55° C. At that temperature, high temperature shrinkable PVC tubing does not shrink further, but on the contrary, cold-flows to relax the compression bond with the connector 12. By overcompressing the connection during the heat-shrink process, the connection 10 will have just the right amount of compression after sterilization.

Figure 2A:
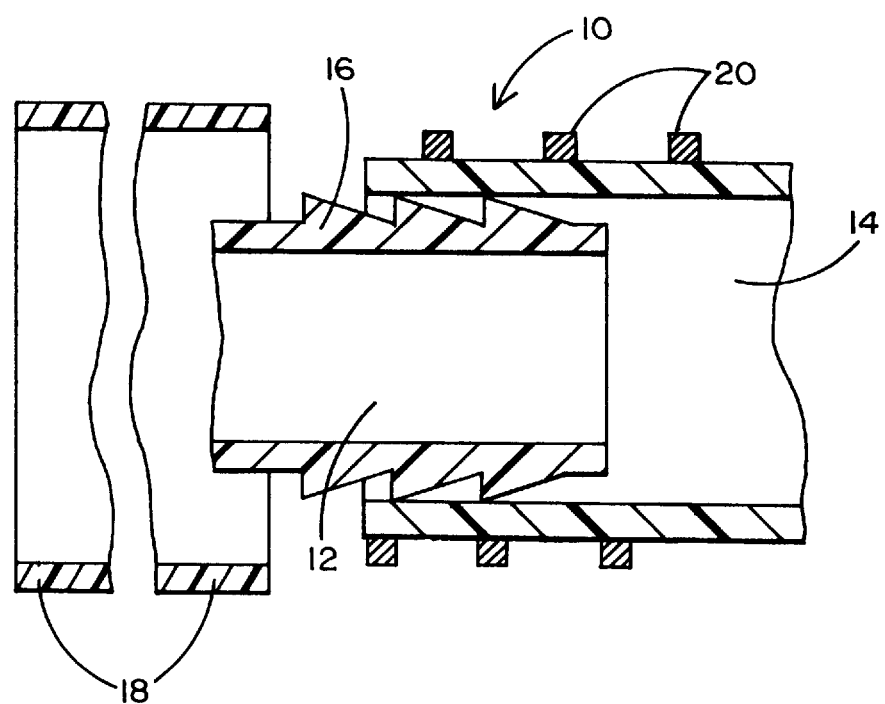
FIGS. 2a and 2b are longitudinal cross sections, respectively, of a connector before and after using another embodiment of the invention.
Figure 2B:
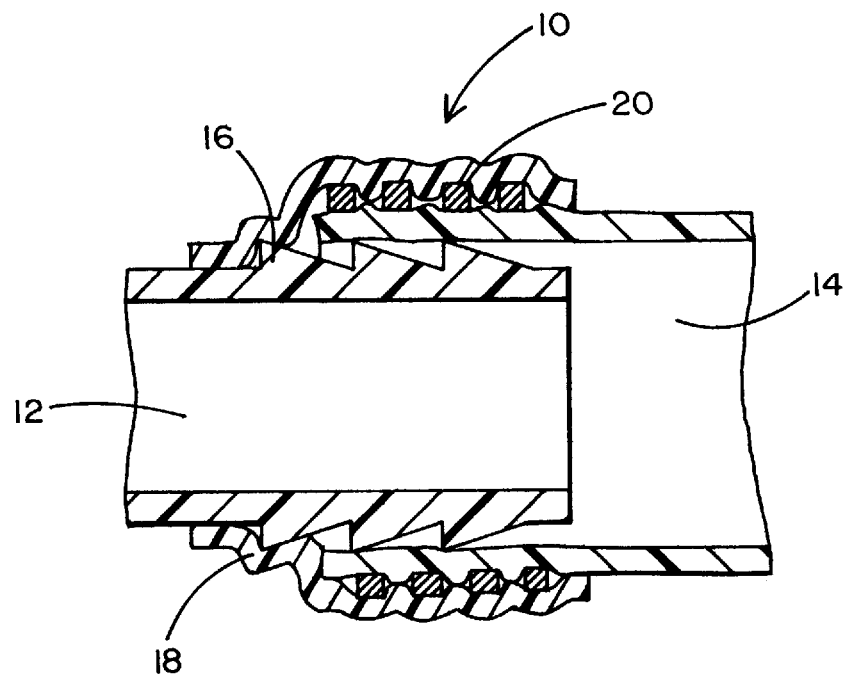

FIGS. 2a and 2b illustrate another embodiment of the invention. In that embodiment, a sleeve 18 of heat-shrink material is first slipped over the connector 12 (FIG. 2a). The tubing 14 is now slipped over the barbs 16, and the sleeve 18 is slipped over both the connector 12 and the tubing 14, care being taken that the left end of sleeve 18 in FIGS. 2a and 2b remains to the left of the leftmost barb 16. If heat is now applied to the sleeve 18, it will shrink to the position shown in FIG. 2b. The left end of the sleeve 18 shrinks onto the connector 12 and the leftmost barb 16, so that the sleeve 18 becomes unable to move to the right. Simultaneously, the shrinking of the right side of the sleeve 18 compresses the tubing 14 against the barbs 16 and secures it to the connector 12.

The sleeve 18 and the tubing 14 may advantageously be anchored to one another by expanding a spring 20, preferably of square cross section, with a relaxed inner diameter somewhat smaller than the outer diameter of tubing 14, and slipping it over the end of tubing 14. The sleeve 18 is then slipped over both the tubing 14 and the spring 20 and is heat-shrunk as described above. The heat shrinking of sleeve 18 and the application of heat to the tubing 14 causes the spring 20 to become pressed both into the tubing 14 and into the sleeve 18, thus anchoring the tubing 14 in the sleeve 18 and tightening it around the connector 12.

The advantage of the latter construction is that conventional nonshrinkable material may be used for the tubing 14 without compromising the integrity of the connection, and that the heat shrinking and sterilization steps may be combined into a single heating. The tubing 14 need only be compressible into firm contact with the barbs 16, so that the connection will be free of leaks. The mechanical anchoring against disengagement of the connector 12 and tubing 14 is provided, when necessary, by the sleeve 18 and spring 20.

It is understood that the exemplary methods and apparatus for connecting PVC tubing to barbed polycarbonate connectors described herein and shown in the drawings represent only presently preferred embodiments of the invention. Indeed, various modifications and additions may be made to such embodiments without departing from the spirit and scope of the invention. Thus, other modifications and additions may be obvious to those skilled in the art and may be implemented to adapt the present invention for use in a variety of different applications.

We claim:

1. A method of assuring secured, sterile connections between rigid barbed connectors on heat-sterilizable medical equipment and sterilizable tubing which heat-shrinks at a temperature higher than the temperature at which said heat sterilization is performed, but cold-flows at said sterilization temperature, comprising the steps of:

a) assembling said connectors and said tubing prior to sterilization;

b) deforming said tubing into a shape providing mechanical engagement with said barbs of said connectors by heat-shrinking said tubing onto said connectors to produce a tight, non-releasable connection;

c) sterilizing said connection;

d) said deforming step involving heat shrinking said tubing sufficiently to shrink said tubing onto said connectors with a shrinking pressure in excess of that needed for use; and e) said sterilizing step involving relaxing said shrinking pressure sufficiently to reduce said shrinking pressure to the level needed for use of said tubing and connectors as a secure sterile fluid-tight connection at room temperature.

2. A method of assuring a secure, sterile connection between a rigid barbed connector formed on a sterilizable medical device and a sterilizable tube, comprising the steps of:

a) pre-assembling said connector and tube;

b) positioning a sleeve of heat-shrink material substantially concentrically around said connector and tubing;

c) interposing a spring between said sleeve and said tubing, said spring being configured to bite into said sleeve and tubing to prevent relative axial movement therebetween when said sleeve is heat-shrunk;

d) heating said sleeve to shrink it into firm engagement with said connector and with said spring and tube; and e) heat-sterilizing said sleeve, spring connector and tube;

f) whereby said tube need only engage said connector enough to prevent leakage.

* * * * *